(12) United States Patent
Reardon et al.

(10) Patent No.: US 10,913,713 B2
(45) Date of Patent: Feb. 9, 2021

(54) METHODS OF PREPARING CYTOTOXIC BENZODIAZEPINE DERIVATIVES

(71) Applicant: IMMUNOGEN, INC., Waltham, MA (US)

(72) Inventors: Michael Reardon, North Attleboro, MA (US); Richard A. Silva, Needham, MA (US)

(73) Assignee: IMMUNOGEN, INC., Waltham, MA (US)

( * ) Notice: Subject to any disclaimer, the term of this patent is extended or adjusted under 35 U.S.C. 154(b) by 0 days.

(21) Appl. No.: 16/679,593

(22) Filed: Nov. 11, 2019

(65) Prior Publication Data
US 2020/0172481 A1   Jun. 4, 2020

Related U.S. Application Data

(60) Provisional application No. 62/758,819, filed on Nov. 12, 2018.

(51) Int. Cl.
*C07D 207/452* (2006.01)
*C07D 487/04* (2006.01)
*C07D 207/448* (2006.01)
*C07D 519/00* (2006.01)

(52) U.S. Cl.
CPC ....... *C07D 207/448* (2013.01); *C07D 519/00* (2013.01)

(58) Field of Classification Search
CPC .................. C07D 207/452; C07D 487/04
See application file for complete search history.

(56) References Cited

FOREIGN PATENT DOCUMENTS

WO    2018/140435 A1    8/2018

OTHER PUBLICATIONS

International Search Report and Written Opinion for Application No. PCT/US2019/060679, dated Feb. 4, 2020, 14 pages.

*Primary Examiner* — Bruck Kifle
(74) *Attorney, Agent, or Firm* — McCarter & English, LLP; Steven G. Davis; Xin Zhang

(57) ABSTRACT

The invention provides novel methods for preparing indolinobenzodiazepine dimer compounds and their synthetic precursors.

20 Claims, No Drawings

METHODS OF PREPARING CYTOTOXIC BENZODIAZEPINE DERIVATIVES

RELATED APPLICATION

This application claims the benefit of the filing date, under 35 U.S.C. § 119(e), of U.S. Provisional Application No. 62/758,819, filed on Nov. 12, 2018. The entire content of the above-referenced application is incorporated herein by reference.

FIELD OF THE INVENTION

The present invention relates to novel methods for preparing cytotoxic indolinobenzodiazepine derivatives.

BACKGROUND OF THE INVENTION

It has been shown that cell-binding agent conjugates of indolinobenzodiazepine dimers that have one imine functionality and one amine functionality display a much higher therapeutic index (ratio of maximum tolerated dose to minimum effective dose) in vivo compared to previously disclosed benzodiazepine derivatives having two imine functionalities. See, for example, WO 2012/128868. The previously disclosed method for making the indolinobenzodiazepine dimers with one imine functionality and one amine functionality involves partial reduction of indolinobenzodiazepine dimers having two imine functionalities. The partial reduction step generally leads to the formation of fully reduced by-product and unreacted starting material, which requires cumbersome purification step and results in low yield.

Thus, there exists a need for improved methods for preparing the indolinobenzodiazepine dimers that are more efficient and suitable for large scale manufacturing process.

SUMMARY OF THE INVENTION

The present invention provides new methods for preparing indolinobenzodiazepine dimer compounds and synthetic precursors thereof.

In one embodiment, the present invention provides a method of preparing a compound of formula (IIIa):

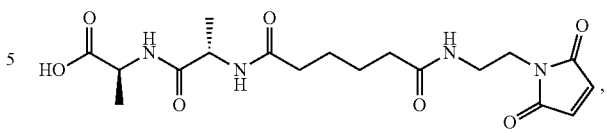

(IIIa)

or a salt thereof, comprising the steps:
(a) reacting a compound of formula (Ia):

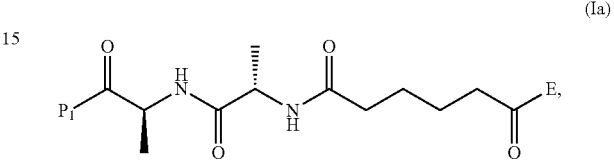

(Ia)

or a salt thereof, with a compound of formula (a):

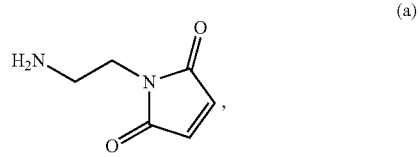

(a)

or a salt thereof, to form a compound of formula (IIa):

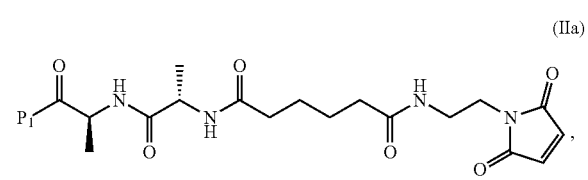

(IIa)

and
(b) reacting the compound of formula (IIa) with a carboxylic acid deprotecting agent to form the compound of formula (IIIa) or a salt thereof, wherein E is —OH, halide or —C(=O)E$_1$ is an activated ester; and P$_1$ is a carboxylic acid protecting group.

In another embodiment, the present invention provides a method of preparing a compound of formula (Va):

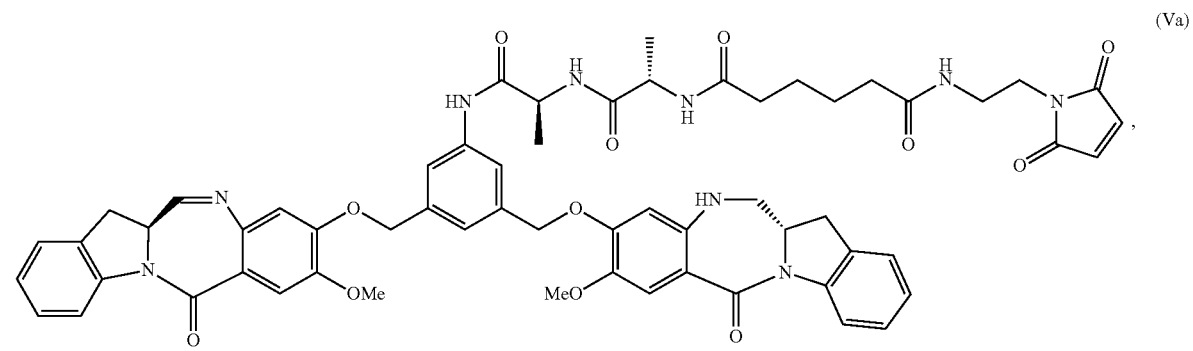 [SMILES: COc1cc2c(cc1OCc1cc(COc3cc4c(cc3OC)C(=O)N3c5ccccc5C[C@H]3CN4)cc(NC(=O)[C@H](C)NC(=O)[C@H](C)NC(=O)CCCCC(=O)NCCN3C(=O)C=CC3=O)c1)N=C[C@@H]1Cc3ccccc3N1C2=O]

(Va)

comprising the steps of:
(a) reacting a compound of formula (Ia):

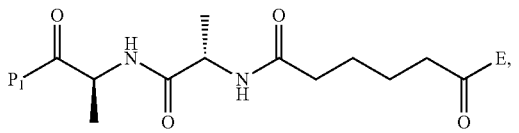

or a salt thereof, with a compound of formula (a):

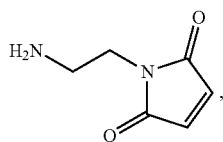

or a salt thereof, to form a compound of formula (IIa):

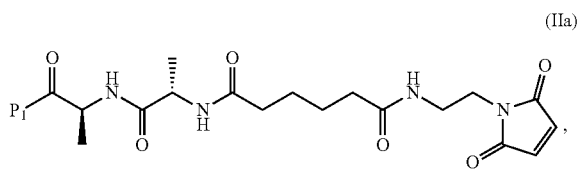

(b) reacting the compound of formula (IIa) with a carboxylic acid deprotecting agent to form the compound of formula (IIIa):

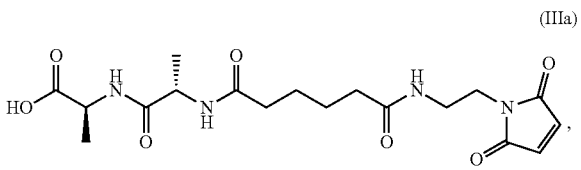 [SMILES: C[C@H](NC(=O)[C@H](C)NC(=O)CCCCC(=O)NCCN1C(=O)C=CC1=O)C(=O)O]

or a salt thereof; and
(c) reacting the compound of formula (IIIa) with a compound of formula (IV):

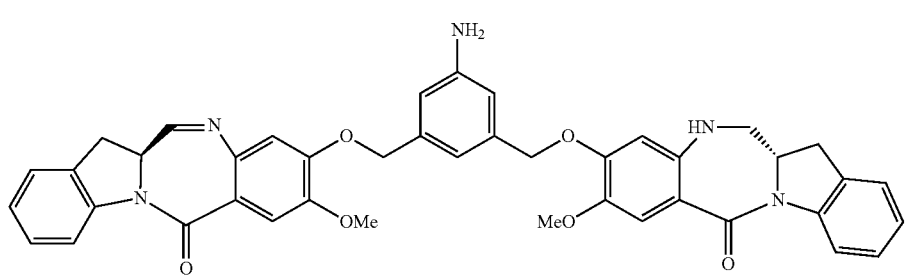

to form the compound of formula (Va), wherein E is —OH, halide or —C(=O)$E_1$ is an activated ester; and $P_1$ is a carboxylic acid protecting group.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention.

It should be understood that any of the embodiments described herein can be combined with one or more other embodiments of the invention, unless explicitly disclaimed or improper. Combination of embodiments are not limited to those specific combinations claimed via the multiple dependent claims.

Definitions

"Alkyl" as used herein refers to a saturated linear or branched monovalent hydrocarbon radical. In preferred embodiments, a straight chain or branched chain alkyl has thirty or fewer carbon atoms (e.g., $C_1$-$C_{30}$ for straight chain alkyl group and $C_3$-$C_{30}$ for branched alkyl), and more preferably twenty or fewer carbon atoms. Even more preferably, the straight chain or branched chain alkyl has ten or fewer carbon atoms (i.e., $C_1$-$C_{10}$ for straight chain alkyl group and $C_3$-$C_{10}$ for branched alkyl). In other embodiments, the straight chain or branched chain alkyl has six or fewer carbon atoms (i.e., $C_1$-$C_6$ for straight chain alky group or $C_3$-$C_6$ for branched chain alkyl). Examples of alkyl include, but are not limited to, methyl, ethyl, 1-propyl, 2-propyl, 1-butyl, 2-methyl-1-propyl, —CH$_2$CH(CH$_3$)$_2$), 2-butyl, 2-methyl-2-propyl, 1-pentyl, 2-pentyl 3-pentyl, 2-methyl-2-butyl, 3-methyl-2-butyl, 3-methyl-1-butyl, 2-methyl-1-butyl, 1-hexyl), 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Moreover, the term "alkyl" as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. As used herein, ($C_x$-$C_{xx}$)alkyl or $C_{x-xx}$alky means a linear or branched alkyl having x-xx carbon atoms.

As used herein, an "activated ester" refers to an ester group that is readily displaced by a hydroxyl or an amine group. Exemplary activated esters include, but are not limited to N-hydroxysuccinimide ester, nitrophenyl (e.g., 2 or 4-nitrophenyl) ester, dinitrophenyl (e.g., 2,4-dinitrophenyl) ester, sulfo-tetraflurophenyl (e.g., 4-sulfo-2,3,5,6-tetrafluorophenyl) ester, pentafluorophenyl ester, nitropyridyl (e.g., 4-nitropyridyl) ester, trifluoroacetate, and acetate.

The term "halide" refers to F, Cl, Br or I. In one embodiment, the halide is Cl. In one embodiment, the halide is Br. In one embodiment, the halide is I. In one embodiment, the halide is F.

The term "compound" is intended to include compounds for which a structure or formula or any derivative thereof has been disclosed in the present invention or a structure or formula or any derivative thereof that has been incorporated by reference. The term also includes, stereoisomers, geometric isomers, or tautomers. The specific recitation of "stereoisomers," "geometric isomers," "tautomers," "salt" in certain aspects of the invention described in this application shall not be interpreted as an intended omission of these forms in other aspects of the invention where the term "compound" is used without recitation of these other forms.

The term "precursor" of a given group refers to any group which may lead to that group by any deprotection, a chemical modification, or a coupling reaction.

The term "chiral" refers to molecules which have the property of non-superimposability of the mirror image partner, while the term "achiral" refers to molecules which are superimposable on their mirror image partner.

The term "stereoisomer" refers to compounds which have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as crystallization, electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds," John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "protecting group" or "protecting moiety" refers to a substituent that is commonly employed to block or protect a particular functionality while reacting other functional groups on the compound, a derivative thereof, or a conjugate thereof.

An "carboxylic acid protecting group" is a substituent attached to an carbonyl group that blocks or protects the carboxylic acid functionality in the compound. Such groups are well known in the art (see for example, P. Wuts and T. Greene, 2007, Protective Groups in Organic Synthesis, Chapter 5, J. Wiley & Sons, NJ). Suitable carboxylic acid protecting group include, but are not limited to, alkyl ester (e.g., methyl ester or tert-butyl ester), benzyl ester, thioester (e.g., tert-butyl thioester), silyl ester (e.g., trimethylsilyl ester), 9-fluorenylmethyl ester, (2-trimethylsilyl)ethoxymethyl ester, 2-(trimethylsilyl)ethyl ester, diphenylmethyl ester or oxazoline. In certain embodiments, the carboxylic acid protecting group is methyl ester, tert-butyl ester, benzyl ester or trimethylsilyl ester. In certain embodiments, the carboxylic acid protecting group is tert-butyl ester.

As used herein, "carboxylic acid deprotecting agent" refers a reagent that is capable of cleaving a carboxylic acid protecting group to form free carboxylic acid. Such reagents are well known in the art (see for example P. Wuts and T. Greene, 2007, Protective Groups in Organic Synthesis, Chapter 5, J. Wiley & Sons, NJ) and depend on the carboxylic acid protecting group used. For example, when the carboxylic acid protecting group is tert-butyl ester, it can be cleaved with an acid. In certain embodiment, the carboxylic acid deprotecting agent is trifluoroacetic acid.

As used herein, "alcohol activating agent" refers a reagent that increases the reactivity of a hydroxyl group thereby making the hydroxyl group a better leaving group. Examples of such alcohol activating agents include p-toluenesulfonyl chloride, thionyl chloride, triflic anhydride, mesyl chloride, mesyl anhydride, triphenylphosphine, acyl chloride, 4-dimethylaminopyridine, and others. In certain embodiments, the alcohol activating agent is thionyl chloride. In certain embodiment, the alcohol activating agent is triphenylphosphine.

The phrase "salt" as used herein, refers to an organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A salt may involve the inclusion of another molecule such as an acetate ion, a succinate ion or other counter ion. The counter ion may be any organic or inorganic moiety that stabilizes the charge on the parent compound. Furthermore, a salt may have more than one charged atom in its structure. Instances where multiple charged atoms are part of the salt can have multiple counter ions. Hence, a salt can have one or more charged atoms and/or one or more counter ion.

If the compound of the invention is a base, the desired salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In certain embodiments, the salt is a pharmaceutically acceptable salt. The phrase "pharmaceutically acceptable" indicates that the substance or composition must be compatible chemically and/or toxicologically, with the other ingredients comprising a formulation, and/or the mammal being treated therewith.

As used herein, the volume amount (V) means the ratio of the solvent volume (in mL) versus the weight amount (in g) of the compound. For example, 40 volume amount means that 40 mL of solvent is used per 1 g of the compound.

METHODS OF THE PRESENT INVENTION

The present invention provides novel synthetic methods for preparing indolinobenzodiazepine dimer compounds and precursors.

In a first embodiment, the present invention provides a method of preparing a compound of formula (III):

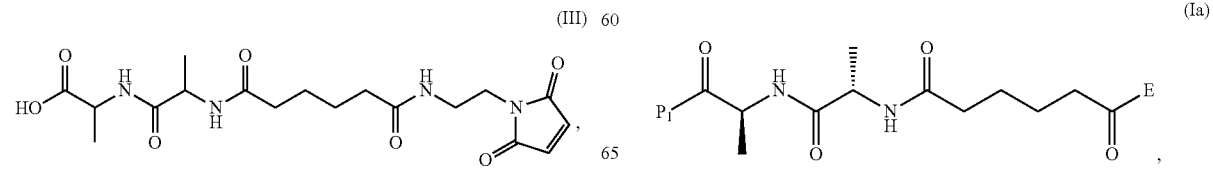

or a salt thereof, comprising the steps:

(a) reacting a compound of formula (I):

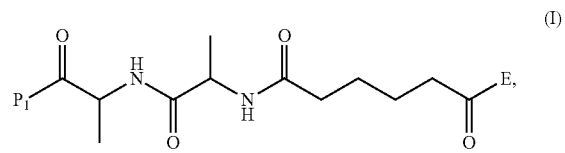

or a salt thereof, with a compound of formula (a):

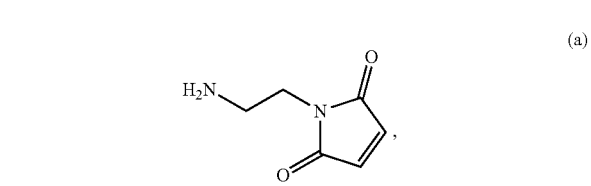

or a salt (e.g., HCl salt or TFA salt) thereof, to form a compound of formula (II):

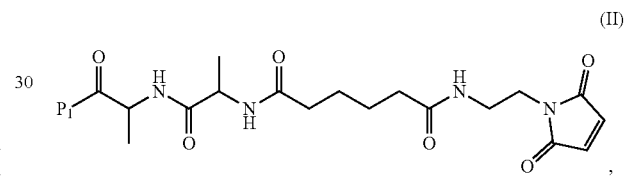

and (b) reacting the compound of formula (II) with a carboxylic acid deprotecting agent to form the compound of formula (III), wherein E is —OH, halide or —C(=O)E is an activated ester; and $P_1$ is a carboxylic acid protecting group.

In a $1^{st}$ specific embodiment, the present invention provides a method of preparing a method of preparing a compound of formula (IIIa):

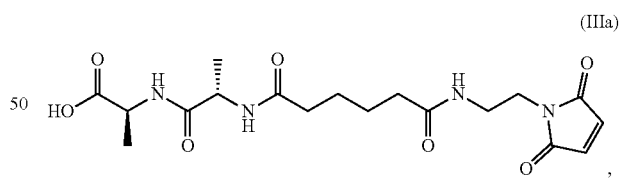

or a salt thereof, comprising the steps:

(a) reacting a compound of formula (Ia):

or a salt thereof, with a compound of formula (a):

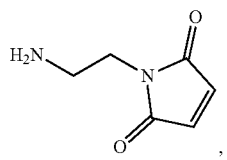
(a)

or a salt (e.g., HCl salt or TFA salt) thereof, to form a compound of formula (IIa):

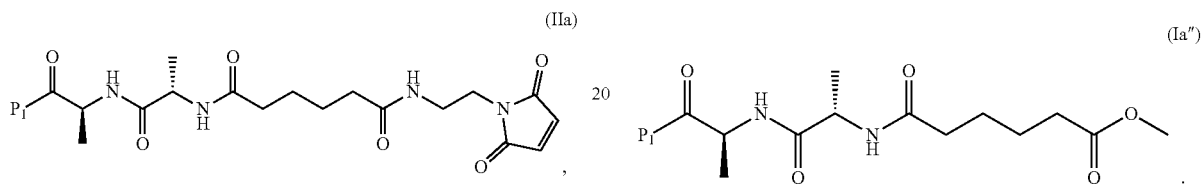
(IIa)

and (b) reacting the compound of formula (IIa) with a carboxylic acid deprotecting agent to form the compound of formula (IIIa), wherein E is —OH, halide or —C(=O)$E_1$ is an activated ester; and $P_1$ is a carboxylic acid protecting group.

In one embodiment, for the method described in the first embodiment or the 1$^{st}$ specific embodiment, E is —OH and the compound of formula (I) or (Ia) is prepared by hydrolysis of the compound of formula (I″) or (Ia″):

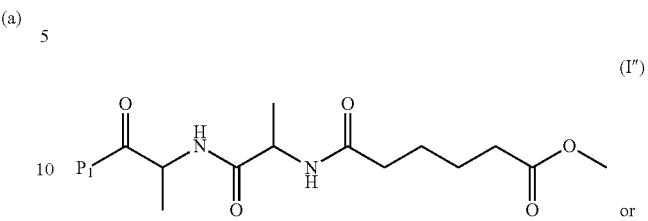

In a specific embodiment, the hydrolysis is performed in the presence of a base. In another specific embodiment, the base is selected from LiOH, KOH, NaOH. In yet another specific embodiment, the base is LiOH.

In a second embodiment, the method of the first embodiment further comprises reacting the compound of formula (III) with a compound of formula (IV):

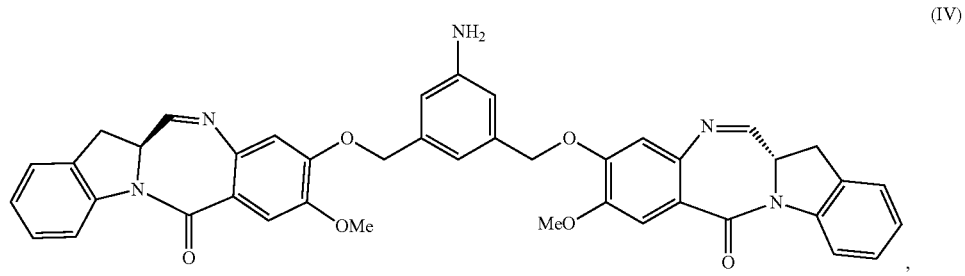 [SMILES: COc1cc2c(cc1OCc1cc(N)cc(COc3cc4c(cc3OC)C(=O)N3c5ccccc5C[C@H]3C=N4)c1)N=C[C@@H]1Cc3ccccc3N1C2=O]
(IV)

to form a compound of formula (V):

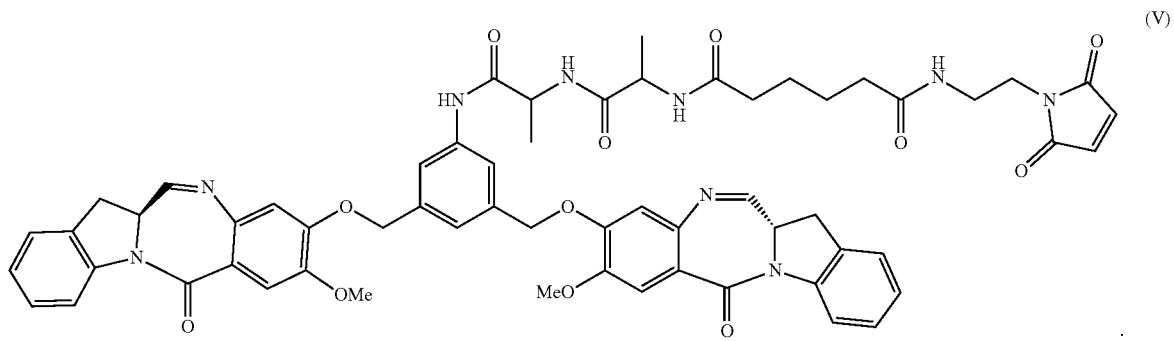 [SMILES: COc1cc2c(cc1OCc1cc(COc3cc4c(cc3OC)C(=O)N3c5ccccc5C[C@H]3C=N4)cc(NC(=O)C(C)NC(=O)C(C)NC(=O)CCCCC(=O)NCCN3C(=O)C=CC3=O)c1)N=C[C@@H]1Cc3ccccc3N1C2=O]
(V)

In a 2nd specific embodiment, the method of the 1st specific embodiment further comprises reacting the compound of formula (IIIa) with a compound of formula (IV):

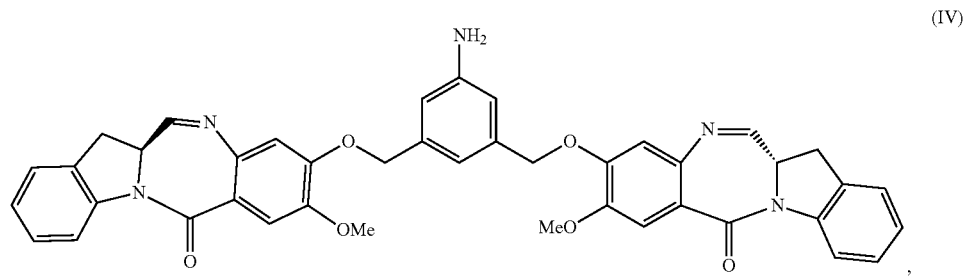 [SMILES: COc1cc2c(cc1OCc1cc(N)cc(COc3cc4c(cc3OC)C(=O)N3c5ccccc5C[C@H]3C=N4)c1)N=C[C@@H]1Cc3ccccc3N1C2=O]

to form a compound of formula (Va):

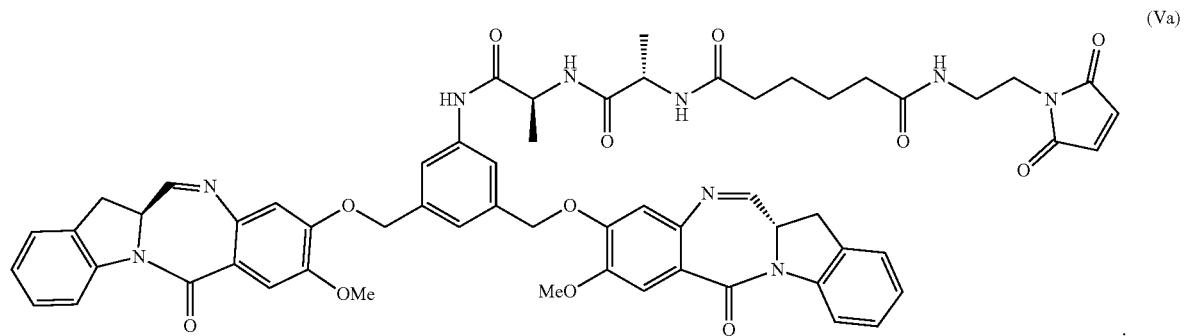 [SMILES: COc1cc2c(cc1OCc1cc(COc3cc4c(cc3OC)C(=O)N3c5ccccc5C[C@H]3C=N4)cc(NC(=O)[C@H](C)NC(=O)[C@H](C)NC(=O)CCCCC(=O)NCCN3C(=O)C=CC3=O)c1)N=C[C@@H]1Cc3ccccc3N1C2=O]

In a third embodiment, the present invention provides a method of preparing a compound of formula (V):

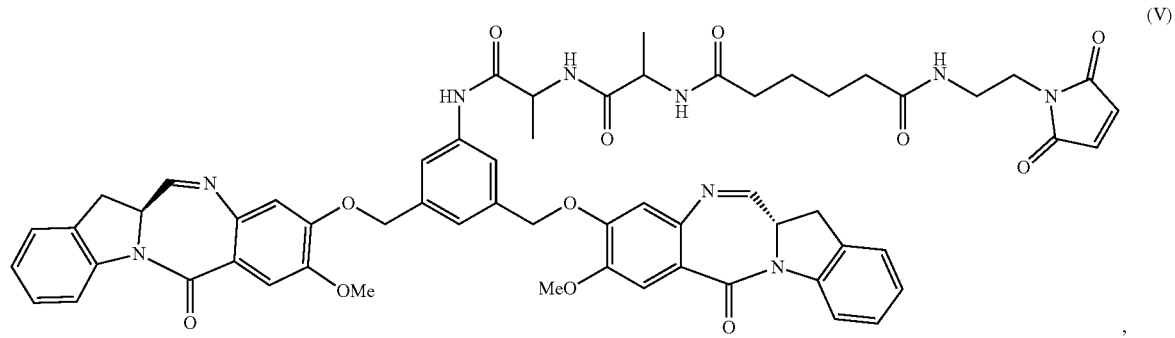 [SMILES: COc1cc2c(cc1OCc1cc(COc3cc4c(cc3OC)C(=O)N3c5ccccc5C[C@H]3C=N4)cc(NC(=O)C(C)NC(=O)C(C)NC(=O)CCCCC(=O)NCCN3C(=O)C=CC3=O)c1)N=C[C@@H]1Cc3ccccc3N1C2=O]

or a salt thereof, with a compound of formula (a):

comprising the steps of:

(a) reacting a compound of formula (I):

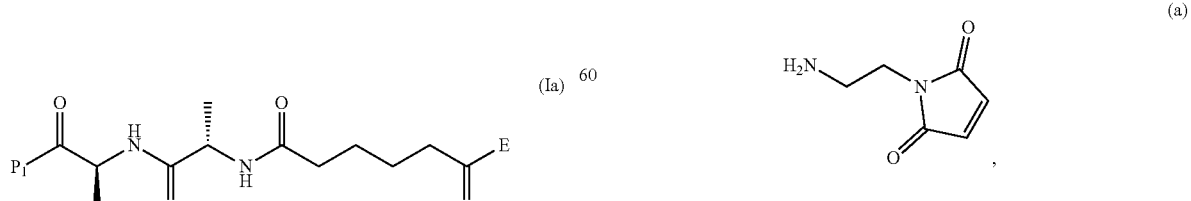

or a salt (e.g., HCl salt or TFA salt) thereof, to form a compound of formula (II):

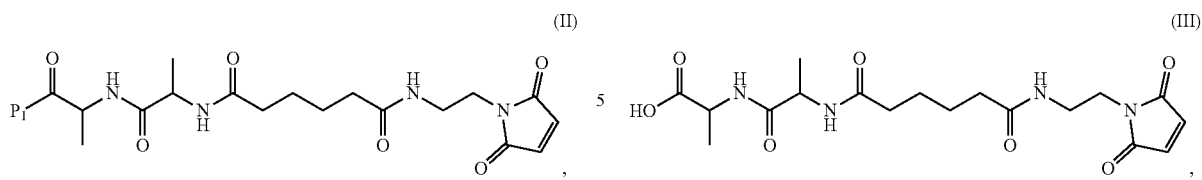

(b) reacting the compound of formula (II) with a carboxylic acid deprotecting agent to form the compound of formula (III):

or a salt thereof; and (c) reacting the compound of formula (III) with a compound of formula (IV):

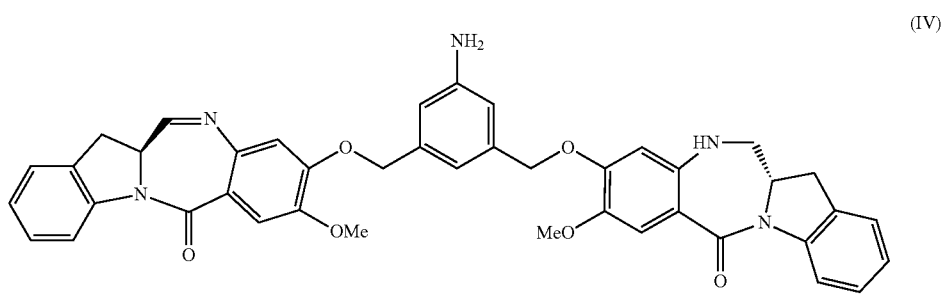 [SMILES: COc1cc2c(cc1OCc1cc(N)cc(COc3cc4c(cc3OC)C(=O)N3c5ccccc5C[C@H]3CN4)c1)N=C[C@@H]1Cc3ccccc3N1C2=O]

to form the compound of formula (V), wherein E is —OH, halide or —C(=O)E$_1$ is an activated ester; and P$_1$ is a carboxylic acid protecting group.

In a 3$^{rd}$ specific embodiment, the present invention provides a method of preparing a compound of formula (Va):

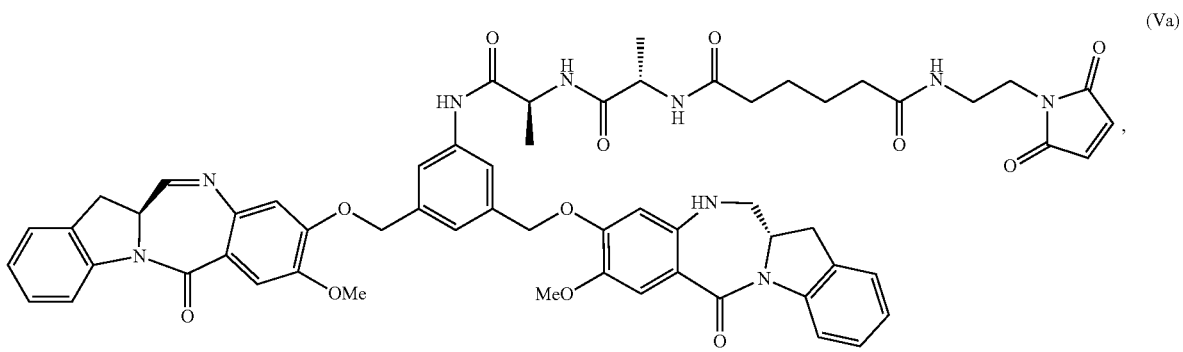 [SMILES: COc1cc2c(cc1OCc1cc(COc3cc4c(cc3OC)C(=O)N3c5ccccc5C[C@H]3CN4)cc(NC(=O)[C@H](C)NC(=O)[C@H](C)NC(=O)CCCCC(=O)NCCN3C(=O)C=CC3=O)c1)N=C[C@@H]1Cc3ccccc3N1C2=O]

comprising the steps of:

(a) reacting a compound of formula (Ia):

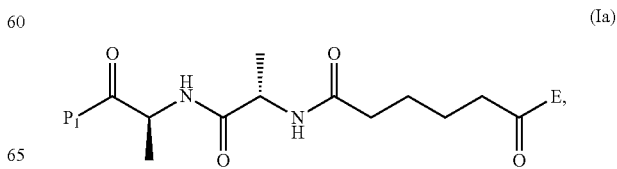

or a salt thereof, with a compound of formula (a):

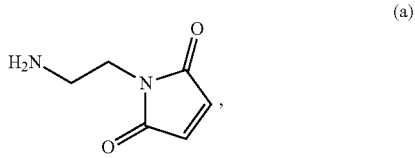

or a salt (e.g., HCl salt or TFA salt) thereof, to form a compound of formula (IIa):

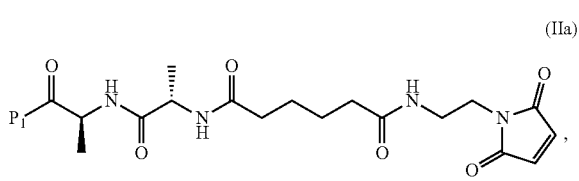

(b) reacting the compound of formula (IIa) with a carboxylic acid deprotecting agent to form the compound of formula (IIIa):

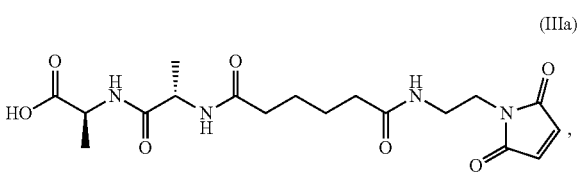 [SMILES: C[C@H](NC(=O)[C@H](C)NC(=O)CCCCC(=O)NCCN1C(=O)C=CC1=O)C(=O)O]

or a salt thereof; and (c) reacting the compound of formula (IIIa) with a compound of formula (IV):

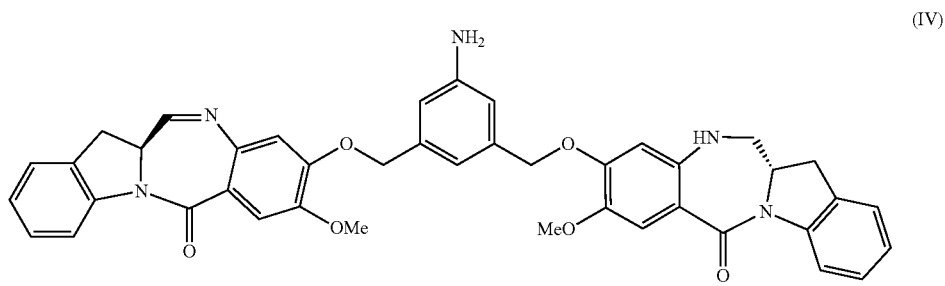 [SMILES: COc1cc2c(cc1OCc1cc(N)cc(COc3cc4c(cc3OC)C(=O)N3c5ccccc5C[C@H]3CN4)c1)N=C[C@@H]1Cc3ccccc3N1C2=O]

to form the compound of formula (Va), wherein E is —OH, halide or —C(=O)$E_1$ is an activated ester; and $P_1$ is a carboxylic acid protecting group.

In a fourth embodiment, for the method described in the first, second or third embodiment or the $1^{st}$, $2^{nd}$ or $3^{rd}$ specific embodiment, $P_1$ can be any suitable carboxylic acid protecting group known in the art. In one embodiment, the carboxylic acid protecting group include, but are not limited to alkyl ester (e.g., methyl ester or tert-butyl ester), benzyl ester, thioester (e.g., tert-butyl thioester), silyl ester (e.g., trimethylsilyl ester), 9-fluorenylmethyl ester, (2-trimethylsilyl)ethoxymethyl ester, 2-(trimethylsilyl)ethyl ester, diphenylmethyl ester or oxazoline. In a specific embodiment, the carboxylic acid protecting group is methyl ester, tert-butyl ester, benzyl ester or trimethylsilyl ester, i.e., $P_1$ is —OMe, —O$^t$Bu, —OBn, —O-silyl (e.g., —OSi(Me)$_3$). In another specific embodiment, the carboxylic acid protecting group is tert-butyl ester, i.e., $P_1$ is —O$^t$Bu.

In a fifth embodiment, for the method described in the first, second, third or fourth embodiment or the $1^{st}$, $2^{nd}$ or $3^{rd}$ specific embodiment, E is —OH and the reaction between the compound of formula (I) or (Ia) or a salt thereof and the compound of formula (a) or a salt (e.g., HCl salt or TFA salt) thereof is carried out in the presence of an activating agent; and the remaining variables are as described in the first, second, third or fourth embodiment or the $1^{st}$, $2^{nd}$ or $3^{rd}$ specific embodiment.

In a specific embodiment, the activating agent is a 2,4,6-trialkyl-1,3,5,2,4,6-trioxatriphosphorinane 2,4,6-trioxide, carbodiimide (e.g., N,N'-dicyclohexylcarbodiimide (DCC) or 1-ethyl-3-(3-dimethylaminopropyl)carbodiimide (EDC)), 1,1'-carbonyldiimidazole (CDI), a uronium, an activated ester, a phosphonium, 2-alkyl-1-alkylcarbonyl-1,2-dihydroquinoline, 2-alkoxy-1-alkoxycarbonyl-1,2-dihydroquinoline, or alkylchloroformate.

In another specific embodiment, the activating agent is 2,4,6-trialkyl-1,3,5,2,4,6-trioxatriphosphorinane 2,4,6-trioxide. In a more specific embodiment, the activating agent is 2,4,6-tripropyl-1,3,5,2,4,6-trioxatriphosphorinane 2,4,6-trioxide (T3P).

In yet another specific embodiment, the activating agent is a 2,4,6-trialkyl-1,3,5,2,4,6-trioxatriphosphorinane 2,4,6-trioxide, 1-[bis(dimethylamino)methylene]-1H-1,2,3-triazolo[4,5-b]pyridinium 3-oxid hexafluorophosphate (HATU), 1-hydroxy-7-azabenzotriazole or 1H-[1,2,3]triazolo[4,5-b]pyridin-1-ol (HOAt), a 2,4,6-trialkyl-1,3,5,2,4,6-trioxatriphosphorinane 2,4,6-trioxide, carbodiimide, a uronium, an activated ester, a phosphonium, 2-alkyl-1-alkylcarbonyl-1,2-dihydroquinoline, 2-alkoxy-1-alkoxycarbonyl-1,2-dihydroquinoline, or alkylchloroformate, or a combination thereof.

In another specific embodiment, the activating agent is 1-[bis(dimethylamino)methylene]-1H-1,2,3-triazolo[4,5-b]pyridinium 3-oxid hexafluorophosphate (HATU). In a more specific embodiment, the activating agents are HATU and HOAt.

Any suitable amount of the activating agent can be used in the reaction between the compound of formula (I) or (Ia) or a salt thereof and the compound of formula (a) or a salt (e.g., HCl salt or TFA salt) thereof. In one embodiment, between 1.0 and 5.0 molar equivalents of the activating agent (e.g., HATU) relative to the amount of the compound of formula (I) or (Ia) is used in the reaction. In a specific embodiment, 1.0-2.0, 1.2-1.7, or 1.3-1.6 equivalent of HATU is used. In a specific embodiment, 1.2, 1.3, 1.4, 1.5, 1.6 or 1.7 equivalents of HATU is used. In a more specific embodiment, 1.5 equivalent of HATU is used.

In one embodiment, the reaction between the compound of formula (I) or (Ia) or a salt thereof and the compound of formula (a) or a salt (e.g., HCl salt or TFA salt) thereof is carried out in the presence of a base. In one embodiment, the base is a non-nucleophilic base. Exemplary non-nucleophilic bases include, but are not limited to, triethylamine, imidazole, diisopropylethylamine, pyridine, 2,6-lutidine, dimethylformamide, 1,8-diazabicyclo[5.4.0]undec-7-ene (DBU), or tetramethylpiperidine. In a specific embodiment, the base is triethylamine or diisopropylethylamine. In another specific embodiment, the base is diisopropylethylamine.

In another embodiment, the reaction between the compound of formula (I) or (Ia) or a salt thereof and the compound of formula (a) or a salt (e.g., HCl salt or TFA salt) thereof is carried out in the presence of an activating agent described above and a base described above. In a specific embodiment, the reaction is carried out in the presence of 2,4,6-tripropyl-1,3,5,2,4,6-trioxatriphosphorinane 2,4,6-trioxide as the activating agent and triethylamine or diisopropylethylamine as the base. In another specific embodiment, the reaction is carried out in the presence of 2,4,6-tripropyl-1,3,5,2,4,6-trioxatriphosphorinane 2,4,6-trioxide (T3P) and diisopropylethylamine. In another specific embodiment, the reaction is carried out in the presence of HATU and HOAt as the activating agents and diisopropylethylamine as the base.

The reaction between the compound of formula (I) or (Ia) or a salt thereof and the compound of formula (a) or a salt (e.g., HCl salt or TFA salt) thereof can be carried out in any suitable organic solvent(s). In one embodiment, the reaction is carried out in dichloromethane.

In another embodiment, the reaction between the compound of formula (I) or (Ia) or a salt thereof and the compound of formula (a) or a salt (e.g., HCl salt or TFA salt) thereof is carried out under an inert atmosphere. In a specific embodiment, the inert atmosphere is achieved by degassing the reaction solutions and purging the reaction vessel with nitrogen or argon.

The reaction between the compound of formula (I) or (Ia) or a salt thereof and the compound of formula (a) or a salt (e.g., HCl salt or TFA salt) thereof can be carried out at a suitable temperature. In some embodiments, the reaction is carried out at a temperature between 0° C. and 50° C., between 5° C. and 50° C., between 10° C. and 50° C., between 10° C. and 40° C., between 10° C. and 30° C. or between 15° C. and 25° C. In more specific embodiments, the reaction is carried out at 20±3° C.

In a sixth embodiment, for the method described in the first, second, third, fourth or fifth embodiment or the 1$^{st}$, 2$^{nd}$ or 3$^{rd}$ specific embodiment, any suitable carboxylic acid protecting group can be used in step (b). Suitable deprotecting agents that can be used depend on the identity of the carboxylic acid protecting group. For example, when $P_1$ is —O$^t$Bu, the protecting group can be removed by the treatment with an acid, a base or a suitable reductant. In certain embodiments, an acid can be used to remove the tert-butyl ester protecting group. Exemplary acids include, but are not limited to, formic acid, acetic acid, trifluoroacetic acid, hydrochloric acid, and phosphoric acid. In a specific embodiment, trifluoroacetic acid is used as the carboxylic acid deprotecting agent.

In one embodiment, the deprotection reaction can be carried in any suitable organic solvent(s). Exemplary organic solvents include, but are not limited to, DMF, CH$_2$Cl$_2$, dichloroethane, THF, dimethylacetamide, methanol, ethanol, etc. In a specific embodiment, the deprotection reaction is carried out in dichloromethane.

In a seventh embodiment, the present invention provides a method of preparing a compound of formula (IIIa):

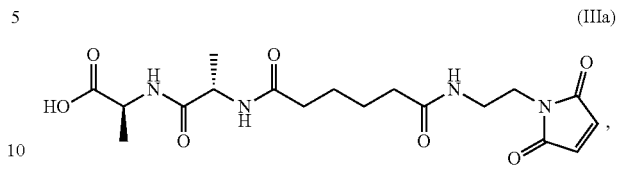

(IIIa)

comprising the steps of:
(a) reacting a compound of formula (Ia1):

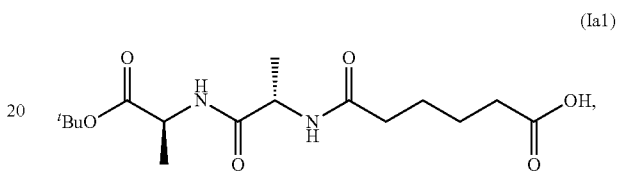

(Ia1)

with a compound of formula (a):

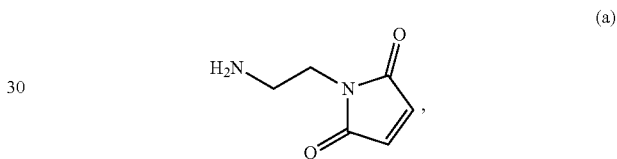

(a)

or a salt (e.g., HCl or TFA salt) thereof, in the presence of an activating agent to form a compound of formula (IIa1):

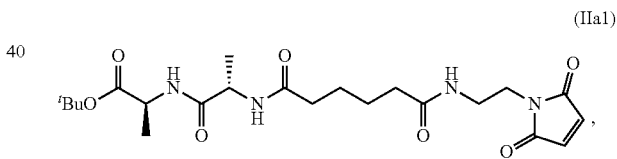

(IIa1)

(b) reacting the compound of formula (IIa1) with a carboxylic acid deprotecting agent to form the compound of formula (IIIa).

In one embodiment, for the method described in the seventh embodiment, the compound of formula Ia1 is prepared by hydrolysis of the compound of formula (Ia1″):

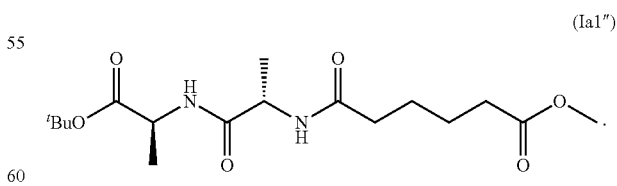

(Ia1″)

In a specific embodiment, the hydrolysis is performed in the presence of a base. In another specific embodiment, the base is selected from LiOH, KOH, NaOH. In yet another specific embodiment, the base is LiOH.

In an eighth embodiment, the present invention provides a method of preparing a compound of formula (Va):

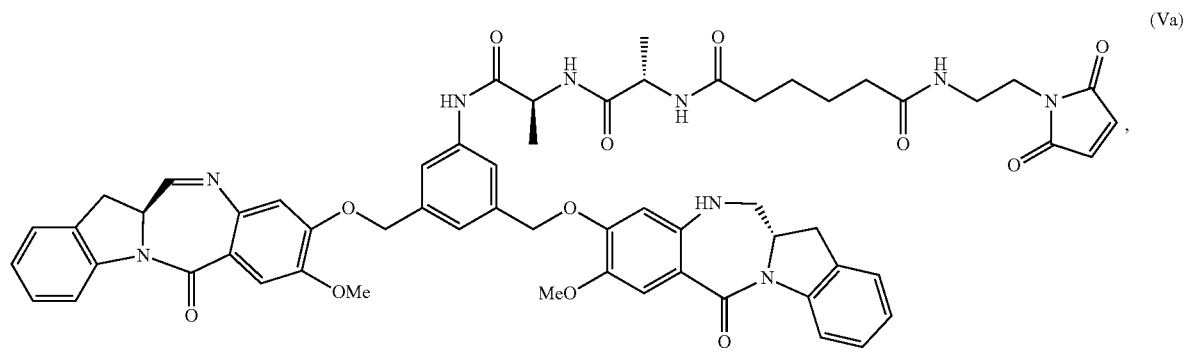 [SMILES: COc1cc2c(cc1OCc1cc(COc3cc4c(cc3OC)C(=O)N3c5ccccc5C[C@H]3CN4)cc(NC(=O)[C@H](C)NC(=O)[C@H](C)NC(=O)CCCCC(=O)NCCN3C(=O)C=CC3=O)c1)N=C[C@@H]1Cc3ccccc3N1C2=O]

(Va)

comprising the steps of:
(a) reacting a compound of formula (Ia1):

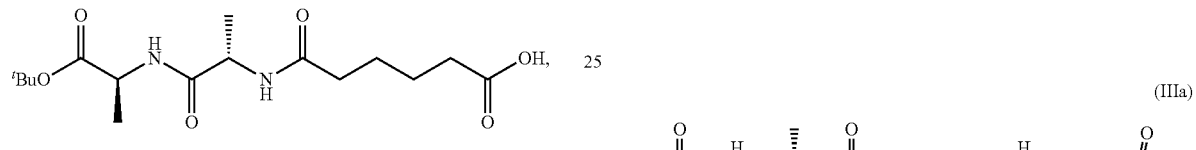

with a compound of formula (a):

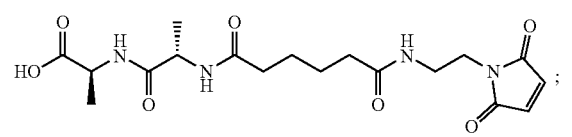

or a salt thereof (e.g., HCl salt or TFA salt), in the presence of an activating agent to form a compound of formula (IIa1):

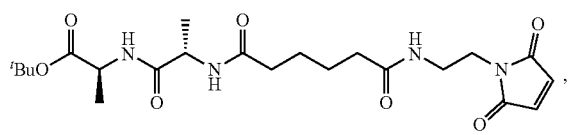

(b) reacting the compound of formula (IIa1) with a carboxylic acid deprotecting agent to form a compound of formula (IIIa):

(IIIa)

and (c) reacting the compound of formula (IIIa) with a compound of formula (IV):

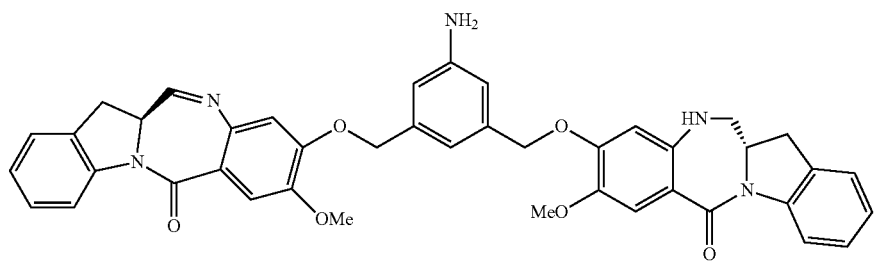

to form the compound of formula (Va).

In a ninth embodiment, for the method of the seventh or eighth embodiment, the reaction of the compound of formula (Ia1) and the compound of formula (a) or a salt (e.g., HCl salt or TFA salt) thereof in step (a) is carried out in the presence of 2,4,6-tripropyl-1,3,5,2,4,6-trioxatriphosphorinane-2,4,6-trioxide (T3P) as the activating agent in step (a). In another embodiment, the reaction of the compound of formula (Ia1) and the compound of formula (a) or a salt (e.g., HCl salt or TFA salt) thereof in step (a) can be carried in the presence of a base. In one embodiment, the base is trimethylamine or diisopropylethylamine. In a specific embodiment, the reaction of the compound of formula (Ia1) and the compound of formula (a) or a salt (e.g., HCl salt or TFA salt) thereof in step (a) can be carried out in the presence of 2,4,6-tripropyl-1,3,5,2,4,6-trioxatriphosphorinane-2,4,6-trioxide (T3P) as the activating agent and diisopropylethylamine as the base. In one embodiment, the reaction can be carried out in dichloromethane.

In a tenth embodiment, for the method described in the seventh, eighth or ninth embodiment, the carboxylic acid deprotecting agent in step (b) is trifluoroacetic acid (TFA). In one embodiment, the deprotection reaction is carried out in dichloromethane.

In an eleventh embodiment, for the method described in the second, third, fourth, fifth, sixth, seventh, eighth, ninth or tenth embodiment or the $2^{nd}$ or $3^{rd}$ specific embodiment, the reaction between the compound of formula (III) or (IIIa) or a salt thereof and the compound of formula (IV) or a salt thereof is carried out in the presence of an activating agent; and the remaining variables are as described in the second, third, fourth, fifth, sixth, seventh, eighth, ninth or tenth embodiment or the $2^{nd}$ or $3^{rd}$ specific embodiment.

In a specific embodiment, the activating agent is a 2,4,6-trialkyl-1,3,5,2,4,6-trioxatriphosphorinane 2,4,6-trioxide, 1-[bis(dimethylamino)methylene]-1H-1,2,3-triazolo[4,5-b]pyridinium 3-oxid hexafluorophosphate (HATU), 1-hydroxy-7-azabenzotriazole or 1H-[1,2,3]triazolo[4,5-b]pyridin-1-ol (HOAt), carbodiimide (e.g., N,N'-dicyclohexylcarbodiimide (DCC) or 1-ethyl-3-(3-dimethylaminopropyl) carbodiimide (EDC)), 1,1'-carbonyldiimidazole (CDI), a uronium, an activated ester, a phosphonium, 2-alkyl-1-alkylcarbonyl-1,2-dihydroquinoline, 2-alkoxy-1-alkoxycarbonyl-1,2-dihydroquinoline, or alkylchloroformate, or a combination thereof.

In another specific embodiment, the activating agent is 1-[bis(dimethylamino)methylene]-1H-1,2,3-triazolo[4,5-b]pyridinium 3-oxid hexafluorophosphate (HATU). In a more specific embodiment, the activating agents are HATU and HOAt.

Any suitable amount of the activating agent can be used in the reaction between the compound of formula (III) or (IIIa) or a salt thereof and the compound of formula (IV) or a salt thereof. In one embodiment, between 1.0 and 5.0 molar equivalents of HATU relative to the amount of the compound of formula (IV) is used in the reaction. In a specific embodiment, 1.0-2.0, 1.2-1.7, or 1.3-1.6 equivalents of HATU is used. In a specific embodiment, 1.2, 1.3, 1.4, 1.5, 1.6 or 1.7 equivalents of HATU is used. In a more specific embodiment, 1.5 equivalent of HATU is used.

In another embodiment, between 0.1 and 1.0 molar equivalent of HOAt relative to the amount of the compound of formula (IV) is used in the reaction between the compound of formula (III) or (IIIa) or a salt thereof and the compound of formula (IV) or a salt thereof. In a specific embodiment, 0.2-0.8, 0.3-0.7 or 0.4-0.6 equivalents of HOAt is used. In another specific embodiment, 0.3, 0.4, 0.5, 0.6 or 0.7 equivalent of HOAt is used. In a more specific embodiment, 0.5 equivalent of HOAt is used.

In one embodiment, the reaction between the compound of formula (III) or (IIIa) or a salt thereof and the compound of formula (IV) or a salt thereof is carried out in the presence of a base. In one embodiment, the base is a non-nucleophilic base. Exemplary non-nucleophilic bases include, but are not limited to, triethylamine, imidazole, diisopropylethylamine, pyridine, 2,6-lutidine, dimethylformamide, 1,8-diazabicyclo[5.4.0]undec-7-ene (DBU), or tetramethylpiperidine. In a specific embodiment, the base is triethylamine or diisopropylethylamine. In another specific embodiment, the base is diisopropylethylamine.

In another embodiment, the reaction between the compound of formula (III) or (IIIa) or a salt thereof and the compound of formula (IV) or a salt thereof is carried out in the presence of an activating agent described above and a base described above. In a specific embodiment, the reaction is carried out in the presence of HATU and HOAt as the activating agents and diisopropylethylamine as the base.

In another embodiment, the reaction between the compound of formula (III) or (IIIa) or a salt thereof and the compound of formula (IV) or a salt thereof is carried out under an inert atmosphere. In a specific embodiment, the inert atmosphere is achieved by degassing the reaction solutions and purging the reaction vessel with nitrogen or argon.

The reaction between the compound of formula (III) or (IIIa) or a salt thereof and the compound of formula (IV) or a salt (e.g., HCl salt or TFA salt) thereof can be carried out in any suitable organic solvent(s). In one embodiment, the reaction is carried out in dichloromethane.

The reaction between the compound of formula (III) or (IIIa) or a salt thereof and the compound of formula (IV) or a salt (e.g., HCl salt, TFA salt) thereof can be carried out at a suitable temperature. In some embodiments, the reaction is carried out at a temperature between 0° C. and 50° C., between 5° C. and 50° C., between 10° C. and 50° C., between 10° C. and 40° C., between 10° C. and 30° C. or between 15° C. and 25° C. In more specific embodiments, the reaction is carried out at 20° C.

In a eleventh embodiment, for the method described in the second, third, fourth, fifth, sixth, eighth, ninth or tenth embodiment or the $2^{nd}$ or $3^{rd}$ specific embodiment, the compound of formula (IV) can be prepared by a method of comprising the step of reacting a compound of formula (V):

(V)

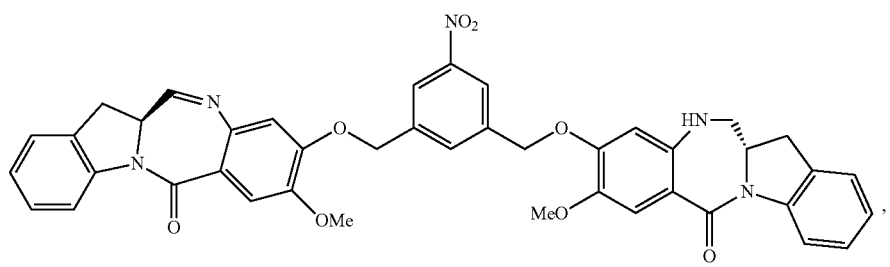

, with a reducing agent to form the compound of formula (IV).

In a twelfth embodiment, for the method described in the second, third, fourth, fifth, sixth, eighth, ninth or tenth embodiment or the 2$^{nd}$ or 3$^{rd}$ specific embodiment, the compound of formula (IV) can be prepared by a method of comprising the steps of:

1) reacting a compound of formula (VI):

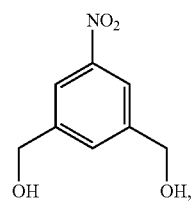
(VI)

with hydrochloric acid in toluene to form a compound of formula (VII):

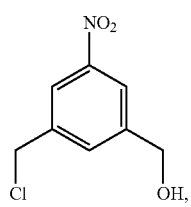
(VII)

2) reacting the compound of formula (VII) with a monomer compound of formula (a1),

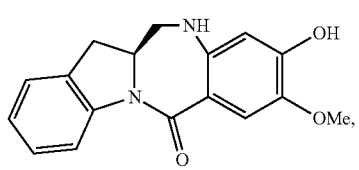
(a1)

to form a compound of formula (VIII):

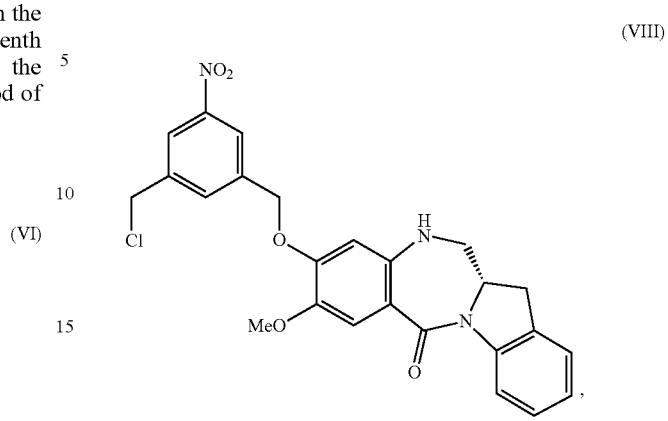
(VIII)

or a salt thereof;

3) reacting the compound of formula (VIII) or a salt thereof with a monomer compound of formula (b1):

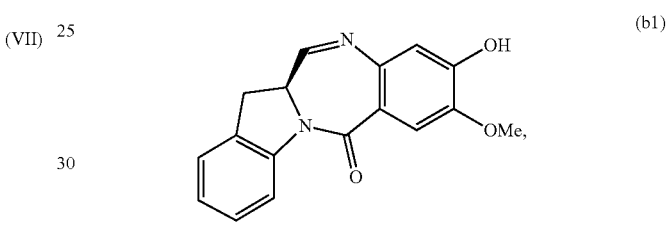
(b1)

to form a compound of formula (V):

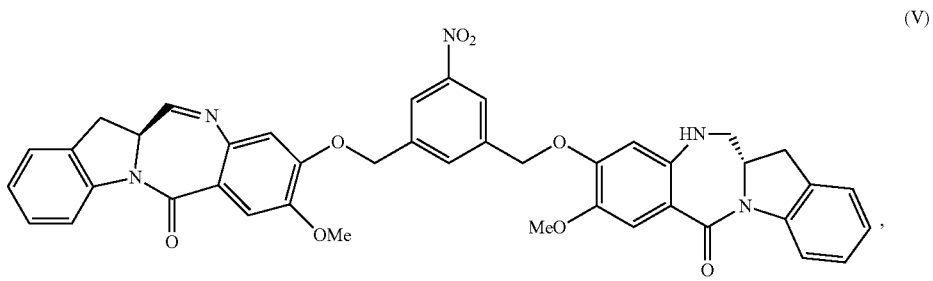 [SMILES: COc1cc2c(cc1OCc1cc(COc3cc4c(cc3OC)C(=O)N3c5ccccc5C[C@H]3CN4)cc([N+](=O)[O-])c1)N=C[C@@H]1Cc3ccccc3N1C2=O]
(V)

or a salt thereof; and 4) reacting the compound of formula (V) or a salt thereof with a reducing agent to form the compound of formula (IV).

In one embodiment, for the method described in the eleventh or twelfth embodiment, any suitable reducing agent that can convert a nitro (—NO$_2$) group to an amine (—NH$_2$) group can be used for converting the compound of formula (V) to the compound of formula (IV). In one embodiment, the reducing reagent is selected from the group consisting of: hydrogen gas, sodium hydrosulfite, sodium sulfide, stannous chloride, titanium (II) chloride, zinc, iron and samarium iodide. In another embodiment, the reducing reagent is Fe/NH$_4$Cl, Fe/NH$_4$Cl, Zn/NH$_4$Cl, FeSO$_4$/NH$_4$OH, or Sponge Nickel. In a specific embodiment, the reducing agent is Fe/NH$_4$Cl.

In one embodiment, for step 1) in the method described in the twelfth embodiment, compound of formula (VI) is reacted with concentrated hydrochloric acid to form the compound of formula (VII).

In another embodiment, for step 2) in the method described in the twelfth embodiment, the compound of formula (VII) is reacted with the monomer compound of formula (a1) in the presence of an alcohol activating agent and an azodicarboxylate. In a specific embodiment, the alcohol activating agent is tributylphosphine or triphenylphosphine. In another specific embodiment, the azodicarboxylate is diethyl azodicarboxylate (DEAD), diisopropyl azodicarboxylate (DIAD), 1,1'-(azodicarbonyl) dipiperidine (ADDP), and ditertbutyl azodicarboxylate (DTAD). In another specific embodiment, the alcohol activating agent is tributylphosphine or triphenylphosphine, and the azodicarboxylate is diethyl azodicarboxylate (DEAD), diisopropyl azodicarboxylate (DIAD), 1,1'-(azodicarbonyl) dipiperidine (ADDP), and ditertbutyl azodicarboxylate (DTAD). In an even more specific embodiment, the alcohol activating agent is tributylphosphine and the azodicarboxylate is DIAD. In another more specific embodiment, the alcohol activating agent is triphenylphosphine and the azodicarboxylate is DIAD. In one embodiment, the triphenylphosphine is added after the mixing of the compound of formula (VII), the monomer compound of formula (a1) and the azodicarboxylate. In an even more specific embodiment, the triphenylphosphine is added after the mixing of the compound of formula (VII), the monomer compound of formula (a1) and DIAD.

In one embodiment, for step 3) in the method described in the twelfth embodiment, the reaction between the compound of formula (VIII) and the monomer compound of formula (b1) is carried out in the presence of a base. In one embodiments, the base is sodium carbonate, potassium carbonate, cesium carbonate, sodium hydride, or potassium hydride. In a specific embodiment, the base is potassium carbonate. In another embodiment, the reaction between the compound of formula (VIII) and the monomer compound of formula (b1) further comprises potassium iodide. In a specific embodiment, the reaction between the compound of formula (VIII) and the monomer compound of formula (b1) is carried out in the presence of potassium carbonate and potassium iodide.

All references cited herein and in the examples that follow are expressly incorporated by reference in their entireties.

EXAMPLES

The following solvents, reagents, protecting groups, moieties and other designations may be referred to by their abbreviations in parenthesis:
eq=molar equivalent
V=volume
DCM or $CH_2Cl_2$=dichloromethane
DIEA or DIPEA=N,N-diisopropylethylamine
g=grams
LCMS=liquid chromatography mass spectrometry
min=minutes
mg=milligrams
mL=milliliters
mmol=millimoles
MS=mass spectrometry
tBME or MTBE=Methyl tert-butyl ether
NMR=nuclear magnetic resonance spectroscopy
T3P=2,4,6-trialkyl-1,3,5,2,4,6-trioxatriphosphorinane 2,4,6-trioxide
TFA=trifluoroacetic acid
ACN=acetonitrile
HATU=1-[bis(dimethylamino)methylene]-1H-1,2,3-triazolo[4,5-b]pyridinium 3-oxid hexafluorophosphate
HAOt=1H-[1,2,3]triazolo[4,5-b]pyridin-1-ol or 1-hydroxy-7-azabenzotriazole

Example 1

Synthesis of (S)-tert-butyl 2-((S)-2-(6-((2-(2,5-dioxo-2,5-dhydro-1H-pyrrol-1-yl)ethyl)amino)-6-oxohexanamido)propanamido)propanoate

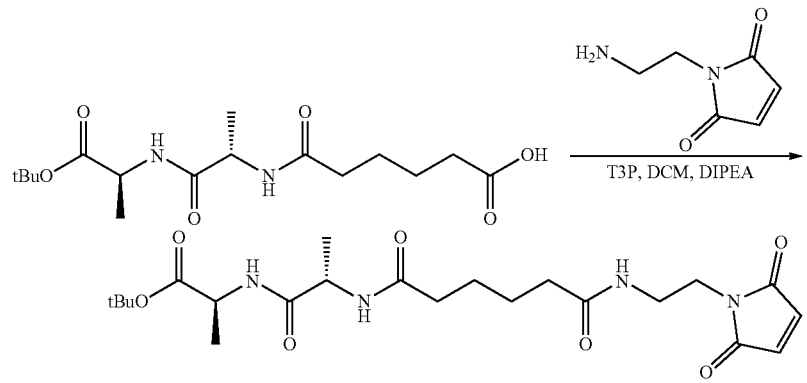

To a clean, dry 100 mL round bottom flask with a stir bar and thermocouple under nitrogen was added —(((S)-1-(((S)-1-(tert-butoxy)-1-oxopropan-2-yl)amino)-1-oxopropan-2-yl)amino)-6-oxohexanoic acid (0.51 g, 1.48 mmol, 1.0 equiv.), 1-(2-aminoethyl)-1H-pyrrole-2,5-dione HCl (0.27 g, 1.53 mmol, 1.1 eq) and dichloromethane (10.0 mL, 20 vol). The resulting mixture was stirred and cooled to 5±3° C. DIPEA (0.760 mL, 4.4 mmol, 3.0 eq) was added to the mixture, followed by the addition of T3P (1.3 mL, 2.22 mmol, 1.5 eq). The reaction mixture was slowly warmed to 20±5° C. and stirred for 2 hours. The reaction was quenched by adding water to the reaction mixture over 30±5 min. The organic phase was separated, washed with semi-saturated brine (2×5.0 mL, 2×10 vol) and water (2×5.0 mL, 2×10 vol), and concentrated. Add toluene to the concentrated organic phase ((2×5.0 mL, 2×10 vol). The resulting solution was concentrated under vacuum to drive off any remaining water. The resulting solid was suspended in DCM (5.0 mL, 10 vol)

and tBME (5.0 mL, 10 vol), stirred at temperature of 5±2° C., and concentrated to dryness to yield the product as white solid (0.557 g, 80.6% yield). Calculated m/z 466.24, found 467.04.

Example 2

Synthesis of (S)-2-((S)-2-(6-((2-(2,5-dioxo-2,5-dhydro-1H-pyrrol-1-yl)ethyl)amino)-6-oxohexanamido)propanamido)propanoic Acid

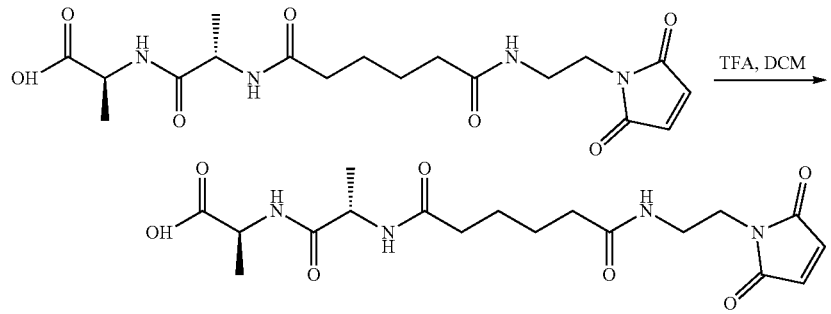

To a clean, dry 100 mL round bottom flask with a stir bar and thermocouple under nitrogen was added (S)-tert-butyl 2-((S)-2-(6-((2-(2,5-dioxo-2,5-dihydro-1H-pyrrol-1-yl) ethyl)amino)-6-oxohexanamido)propanamido)propanoate (0.41 g, 0.88 mmol, 1.0 eq.), followed by dichloromethane (4.0 mL, 10 vol). The resulting mixture was stirred to form a suspension, followed by cooling to 5±3° C. TFA (4.0 mL, 10 vol) was added and the reaction was stirred and allowed to slowly warm to 20±5° C. The reaction was stirred at 20±5° C. for 2 hours and quenched with water (few drops added by glass pipette). The reaction mixture was concentrated to dryness and toluene was added. The resulting toluene solution was concentrated to remove any remaining water. The resulting solid was suspended in dichloromethane (5.0 mL, 10 vol) and tBME (5.0 mL, 10 vol), stirred at temperature of 5±2° C. and concentrated to dryness to afford the product (S)-tert-butyl 2-((S)-2-(6-((2-(2,5-dioxo-2,5-dhydro-1H-pyrrol-1-yl)ethyl)amino)-6-oxohexanamido) propanamido)propanoate (0.557 g, 80.6% yield) as white solid. Calculated m/z 410.18, found 410.99.

Example 3

Synthesis of (S)-9-((3-(chloromethyl)-5-nitrobenzyl) oxy)-8-methoxy-11,12,12a,13-tetrahydro-6H-benzo [5,6][1,4]diazepino[1,2-a]indol-6-one

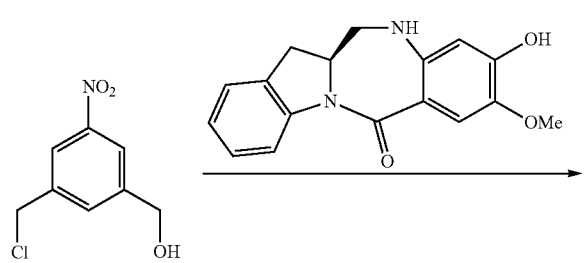

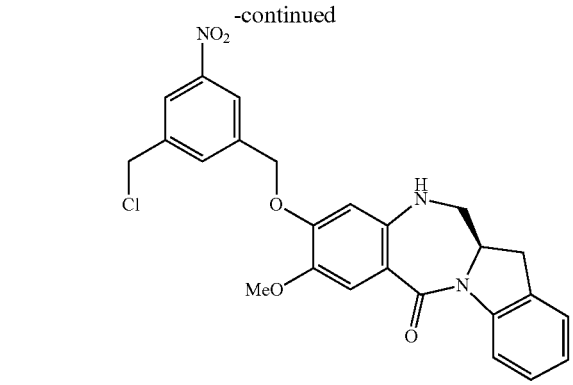

To a dry 100 mL round bottom flask equipped with a stir bar and thermocouple under nitrogen was added (S)-9-hydroxy-8-methoxy-11,12,12a,13-tetrahydro-6H-benzo[5, 6][1,4]diazepino[1,2-a]indol-6-one (1.0 g, 3.375 mmol, 1.0 eq.), followed by terahydrofuran (10.0 mL, 10 V). The mixture was stirred at 20° C.±5° C. to obtain a slightly cloudy solution. 3-(chloromethyl)-5-nitrophenyl)methanol (0.849 g, 4.22 mmol) was then added to the solution and the reaction mixture was stirred at 20° C.±5° C. to obtain a slightly cloudy solution. The reaction was cooled to 5±3° C. and diisopropyl azodicarboxylate (0.930 mL, 4.725 mmol) was added dropwise via addition funnel over 10±2 minutes. Triphenylphosphine (1.24 g, 7.425 mmol) was dissolved in THF (3 mL, 2.4 V) and the resulting solution was added to reaction mixture dropwise to maintain temperature ≤10° C. The reaction mixture was stirred at 5±3° C. for 30 minutes before it was cooled to 5±3° C. and water (5.0 mL, 5V) was added. The resulting mixture was stirred for 30 minutes and DCM (40 mL, 40V) was added. The resulting mixture was transferred to a 250 mL separatory funnel and washed with water (2×10 mL, 2×10V). The organic phase was separated and concentrated to obtain crude product, which was purified via silica gel column chromatography eluted with a gradient of 0-20% DCM/ethyl acetate over 40 minutes. Fractions containing pure products were combined and concentrated to dryness to afford the desired product. Dissolve the concentrated fractions in ethyl acetate and drip into stirring t-butyl methylether (36.0 mL, 18V) and white/orange solid was formed. The mixture was cooled to 5±5° C. and stirred for 2 hours. The solid was filtered to afford the product (1.08 g, 66.6% yield).
Example 4
Synthesis of Compound Va
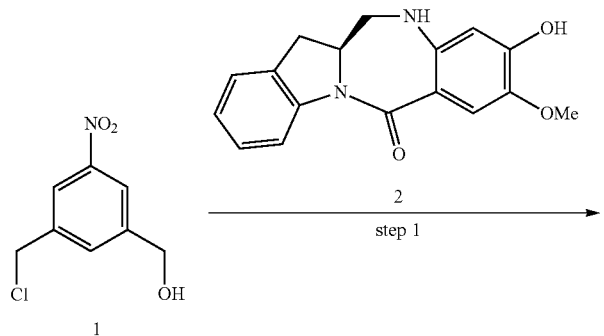
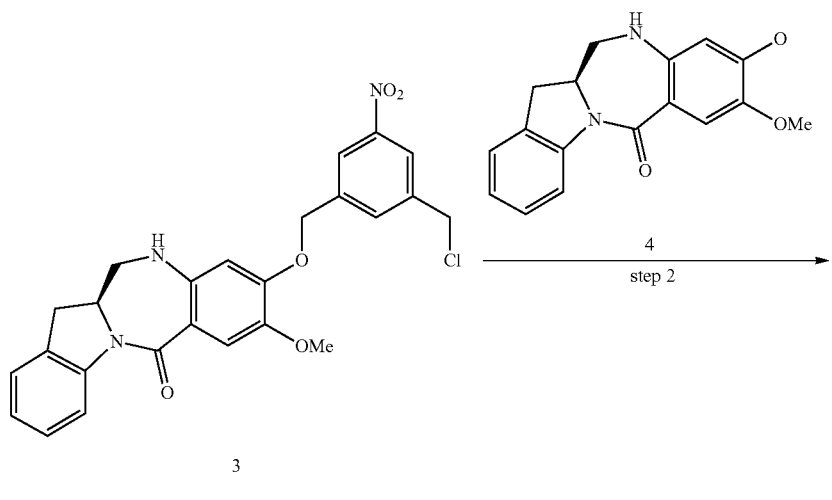
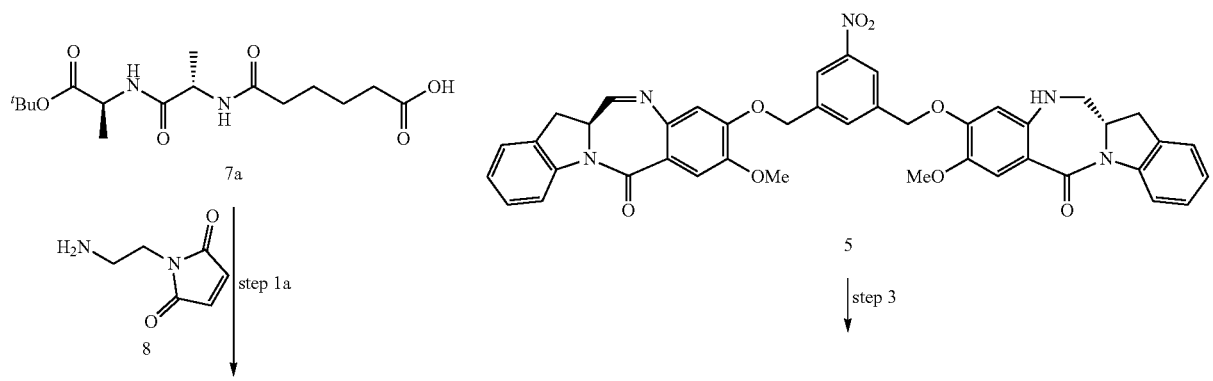

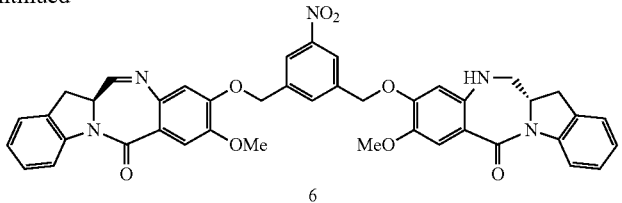

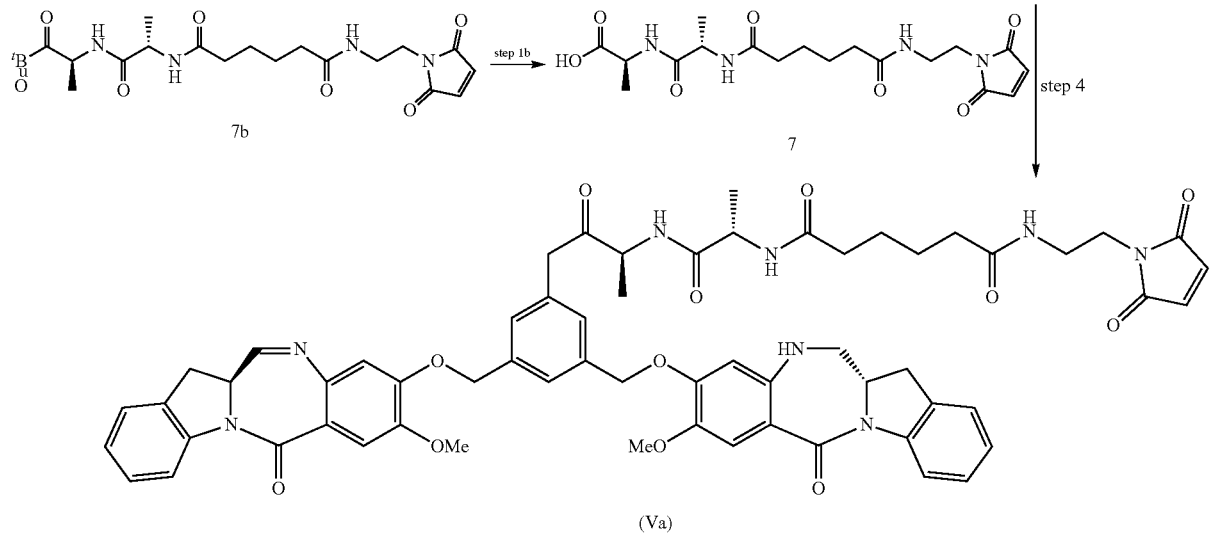

Step 1a

DCM (~1.5V) was loaded followed by compound 7a (8.6 g, 1 eq.) and rinsing with DCM (14.5 V). Maleimide compound 8 was added and DCM (4V) was used for rinsing. The solution was cooled down to 5° C. DIPEA followed by T3P were slowly added and the reaction mixture was stirred at 20° C. After 1 h and 30 minutes, the conversion rate was determined to be 99.4%. The reaction mixture was cooled to 10° C. and quenched by slow addition of water (20V). After phase separation, the aqueous phase is back extracted with DCM (3×20V). The organic phases were combined and washed NaCl 15% solution (2×10V). Crude product 7b was stored at 5° C. before being used for the synthesis of compound 7.

Step 1b

Crude product 7b from step 1a was concentrated to 10V (compared to theoretical yield of 11.65 g). The temperature of the mixture was decreased to 5° C. TFA was slowly added at 5° C. and the reaction mixture was allowed to warm up to 20° C. and stirred. After 1 h, the conversion rate was determined to be 99.6%. The reaction was quenched by addition of water (1V) and concentrated to dryness. Co-evaporation with DCM was performed (3×30V). The residue is dissolved in DCM (13V) and slowly added onto MTBE (13V). The mixture temperature was decreases to 5° C. and the suspension was stirred at 5° C. for 30 minutes before being filtered. The solid was washed with MTBE (2×2.5V) before being dried under deep vacuum at 35° C.

Step 1

Compound 2 (1 eq.) was suspended in THF (10V) and compound 1 (1.25 eq.) was added. The reaction mixture was coiled down to 5° C. and DIAD (1.4 eq.) was added in order to not exceed 10° C. in the mass. PPh$_3$ (1.4 eq.) was dissolved in THF (2V) and slowly added to the reaction mixture in order not to exceed 10° C. in the mass. The reaction mixture was stirred at 5° C. for 30 minutes. The reaction mixture was quenched by adding water (5V) and the mixture was stirred for 30 minutes at 5° C. The reaction mixture was allowed to warm up and stirring was stopped. After separation of the phases, the aqueous phase is extracted with DCM (20 V). Organic phases were combined and washed with water (2×10V), followed by concentration and azeotropic distillation with DCM (2×20V). The mixture was concentration to 10V and the solution of crude product 3 was purified by reverse phase chromatography using YMC C18 Triart column eluting with ACN/water 55/45 v/v. The main peak was collected and the collected fraction was extracted with DCM. The extracted fractions were pooled and concentrated to 10V.

Step 2.

Compound 3 (12.1 g, 1 eq.) in DCM/ACN solution from step 1 was diluted in DMF (17V) at room temperature. The solution was then concentrated to around 17V and transferred to a reactor (ringing with DMF (3V)). Compound 4 (7.8 g, 1.05 eq.) was added, followed by KI (2.09 g, 0.5 eq.) and K$_2$CO$_3$ (7.0 g, 2 eq.). The reaction mixture was stirred at 35° C. for 4 hrs. Another 0.1 eq. of compound 4 was added and the reaction was stirred at 35° C. for 45 minutes. The reaction mixture was cooled to 20° C. and DCM was added (40V) followed by water (20V). The phases were separated and the aqueous phase was back extracted with DCM (20V). The organic phases were combined and washed with NaCl 15% solution (2×20V) followed by water (2×20V). The organic phase is concentrated to 10V and azeotropic distillation was performed with DCM (2×20V). The organic solution was finally concentrated to around 10V (calculated yield 77.7%).

Step 3.

Compound 5 (18.6 g, 1 eq.) was dissolved in THF/MeOH/water (12.5V/1.7V/0.85V) at room temperature and transferred to a reactor. To the reactor, $NH_4Cl$ (14.2 g, 10.5 eq.) and then Fe (7.9 g, 5.6 eq.) were added. The reaction mixture was stirred at 60° C. for 1 hr. The reaction was cooled to 20° C. and diluted with DCM and filtered through Celite and washed with DCM. After concentration to dryness, the residue was dissolved in DCM (20V). The organic phase was washed with saturated NaCl solution (20V) followed with water (2×10V). The organic phase was concentrated and co-evaporated with DCM (2×20V). The crude product was purified by normal phase silica gel chromatography using Dalso SP-100-10-P column eluting with DCM/MEOH gradient from 2.4% MeOH with slope at 0.34%. The combined fractions were concentrated to almost dryness (calculated yield 47.6%).

Step 4

Compound 7 (1.2 eq.) was suspended in DCM (24V) and EEDQ (2.5 eq.) was added. The mixture was stirred for 30 minutes at 20° C. MeOH (5V) was added and the mixture was stirred for 5 minutes at 20° C. Compound 6 (1 eq.) was dissolved in DCM (12V) and the solution was added to the reaction mixture of compound 7 and EEDQ. The reaction mixture was stirred at 20° C. until the conversion rate is 95% or higher. The reaction mixture was washed with 1% NaCl solution (14V). After phase separation, the organic phase was concentrated and co-evaporated with DCM (3×10V). Crude compound Va was dissolved in in DCM/MeOH 97.5/2.5 v/v and purified by silica gel chromatography (Daiso SP-100-10-P) eluting with DCM/MeOH gradient from 5% to 10% MeOH. The combined fractions were concentrated and co-evaporated with DCM to 10V. The solution was concentrated and the residue was dissolved in DMSO and purified by reverse phase chromatography (YMC C18 Triart) eluting with ACN/water 45/55 v/v. Fractions containing the product were extracted in DCM (0.4V) and washed with $NaHCO_3$ 0.5% solution (0.4V) followed by water (2×0.4V). Combined fractions were concentrated and co-evaporated with DCM to almost dryness. The resulting residue was suspended in DCM and transferred to precipitation reaction (75V, including rinsing with DCM). Heptane (75V) was slowly added and the slurry was further stirred at room temperature for 30 minutes. After filtration, the solid was rinsed with DCM/Heptane 1/1 v/v followed by heptane. The solid was dried at 35° C. under deep vacuum.

Example 5

Synthesis of Compound (Va)

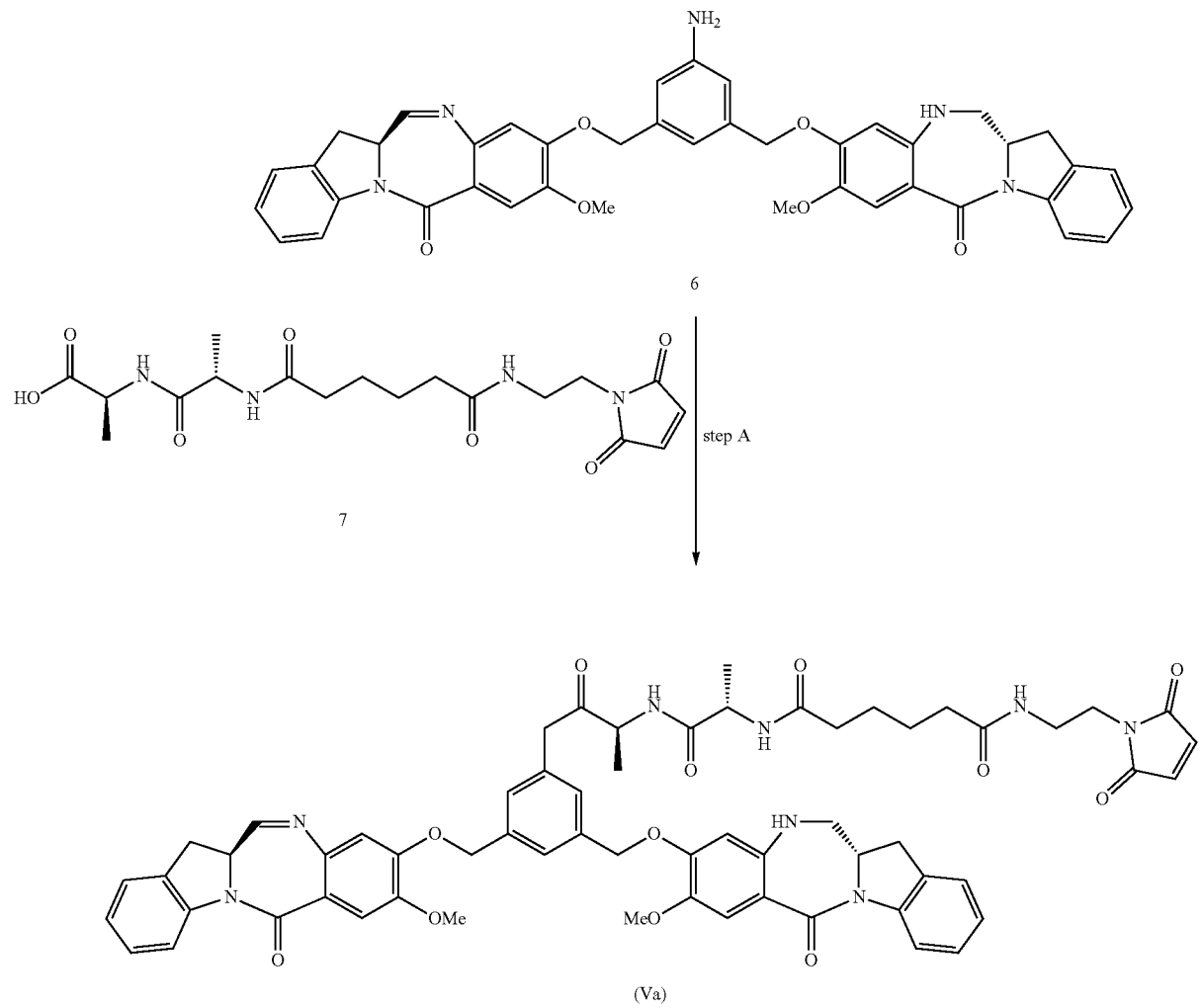

To a clean, dry 100 mL round bottom flask (RBF) under nitrogen atmosphere was charged compound 7 (0.640 g, 1.528 mmol), followed by HATU (0.587 g, 1.529 mmol), HOAt (0.587 g, 1.529 mmol.) and DCM (12 mL, 15 vol). The mixture was stirred for 5±2 minutes at 20° C.±5° C. Compound 6 (0.82 g, 1.020 mmol) was dissolved in DCM (8.2 mL, 10 vol) and the solution was added to the reaction mixture of compound 7, HATU and HOAt. MeOH (0.5 mL, 0.6 vol) was then added. The reaction vessel was degassed and purged with nitrogen. DIPEA (0.268 ml, 1.529 mmol.) in DCM (4.1 ml, 5 vol) was added slowly to the reaction solution. The mixture was stirred for 30±5 minutes at 20° C.±5° C. To the reaction mixture was added neutralized DCM (8.2 mL, 10 vol, pre-washed with sodium bicarbonate solution), followed by 5% sodium carbonate solution (12.3 mL, 15 vol). The resulting solution was stirred at 20° C.±5° C. for 30±5 minutes and then transferred to a separatory funnel and neutralized DCM (12 mL, 15 vol) was added. The solution was mixed by degassing and then allowed to separate for 10±5 minutes. The organic phase was concentrated and purified by reverse phase chromatography (YMC C18 Triart) eluting with a gradient of 5-60% acetonitrile/ deionized water in 20 minutes followed by holding at 60% for 10 minutes, ramping up gradient to 95% in 10 minutes, and holding at 95% for 5 minutes. Fractions containing the product were combined and extracted with DCM (0.7×total volume of fractions). The organic layer was collected and solvent was removed by distillation to afford dry off-white, fine powder product compound (Va) (0.6062 g, 0.529 mmol, 51.9% yield).

The invention claimed is:

1. A method of preparing a compound of formula (IIIa):

(IIIa)

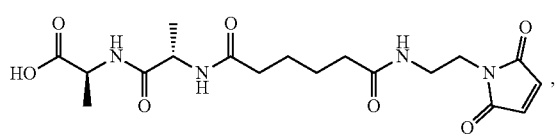

or a salt thereof, comprising the steps:

(a) reacting a compound of formula (Ia):

(Ia)

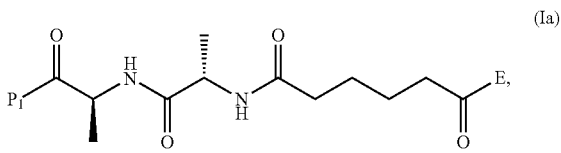

or a salt thereof, with a compound of formula (a):

(a)

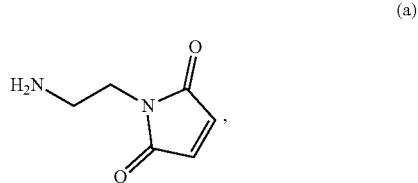

or a salt thereof, to form a compound of formula (IIa):

(IIa)

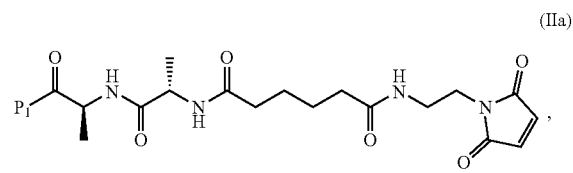

(b) reacting the compound of formula (IIa) with a carboxylic acid deprotecting agent to form the compound of formula (IIIa), wherein E is —OH, halide or —C(=O)E is an activated ester; and $P_1$ is a carboxylic acid protecting group.

2. The method of claim 1, wherein the method further comprises reacting the compound of formula (IIIa) with a compound of formula (IV):

(IV)

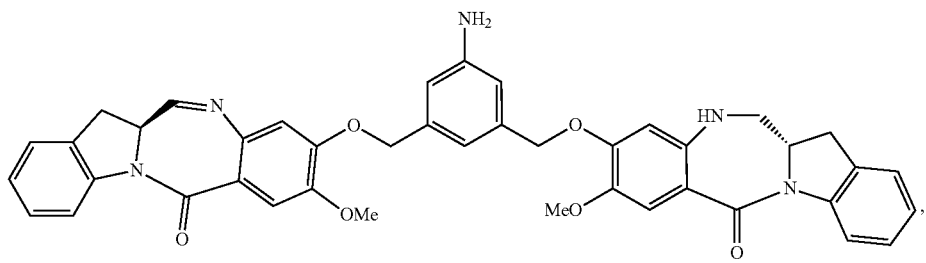

to form a compound of formula (Va):

(Va)

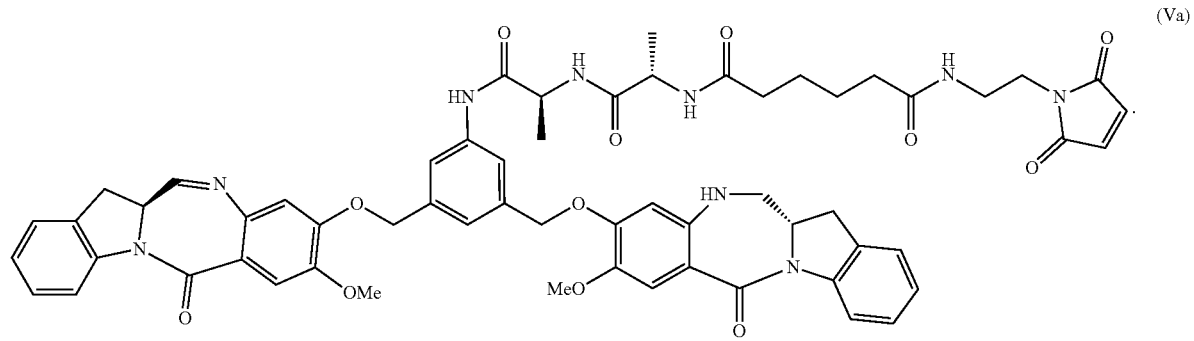 [SMILES: COc1cc2c(cc1OCc1cc(COc3cc4c(cc3OC)C(=O)N3c5ccccc5C[C@H]3CN4)cc(NC(=O)[C@H](C)NC(=O)[C@H](C)NC(=O)CCCCC(=O)NCCN3C(=O)C=CC3=O)c1)N=C[C@@H]1Cc3ccccc3N1C2=O]

3. The method of claim 1, wherein $P_1$ is —O$^t$Bu, —OMe, —OBn, or —O-silyl.

4. The method of claim 3, wherein $P_1$ is —O$^t$Bu.

5. The method of claim 1, wherein E is —OH and the reaction between the compound of formula (Ia) and the compound of formula (a) is carried out in the presence of an activating agent.

6. The method of claim 5, wherein the activating agent is a 2,4,6-trialkyl-1,3,5,2,4,6-trioxatriphosphorinane 2,4,6-trioxide, carbodiimide, a uronium, an activated ester, a phosphonium, 2-alkyl-1-alkylcarbonyl-1,2-dihydroquinoline, 2-alkoxy-1-alkoxycarbonyl-1,2-dihydroquinoline, or alkylchloroformate.

7. The method of claim 6, wherein the activating agent is 2,4,6-tripropyl-1,3,5,2,4,6-trioxatriphosphorinane-2,4,6-trioxide.

8. The method of claim 1, wherein the carboxylic acid deprotecting agent in step (b) is an acid.

9. The method of claim 8, wherein the acid is trifluoroacetic acid (TFA).

10. The method of claim 1, wherein the method comprises the steps of:

(a) reacting a compound of formula (Ia1):

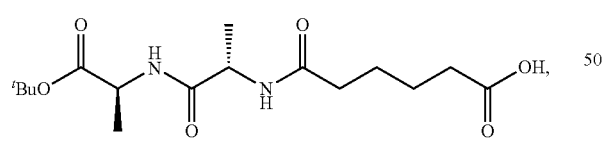

(Ia1)

or a salt thereof, with a compound of formula (a):

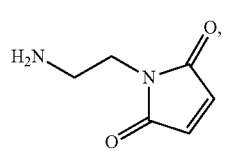

(a)

or a salt thereof, in the presence of an activating agent to form a compound of formula (IIa1):

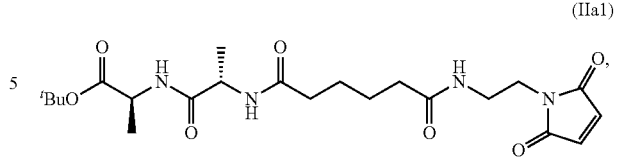

(IIa1)

(b) reacting the compound of formula (IIa1) with a carboxylic acid deprotecting agent to form the compound of formula (IIIa).

11. A method of preparing a compound of formula (Va):

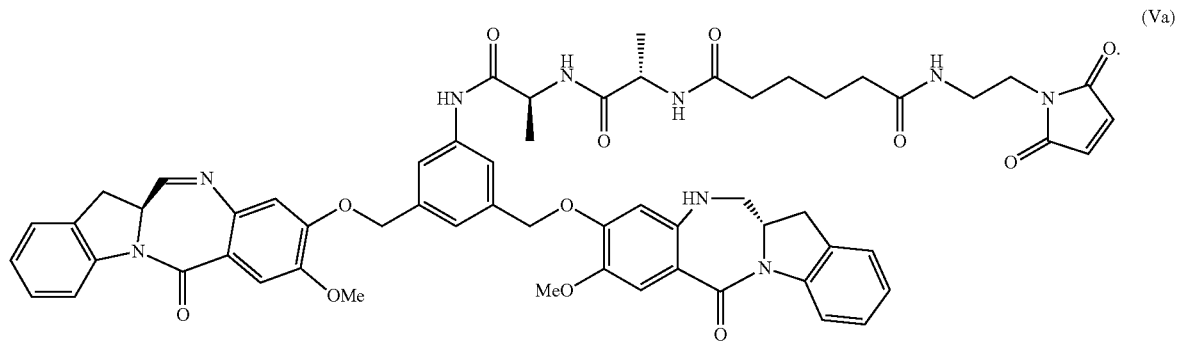 [SMILES: COc1cc2c(cc1OCc1cc(COc3cc4c(cc3OC)C(=O)N3c5ccccc5C[C@H]3CN4)cc(NC(=O)[C@H](C)NC(=O)[C@H](C)NC(=O)CCCCC(=O)NCCN3C(=O)C=CC3=O)c1)N=C[C@@H]1Cc3ccccc3N1C2=O]

(Va)

comprising the steps of:

(a) reacting a compound of formula (Ia):

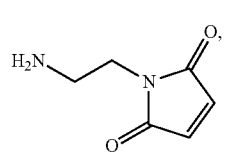

(Ia)

or a salt thereof, with a compound of formula (a):

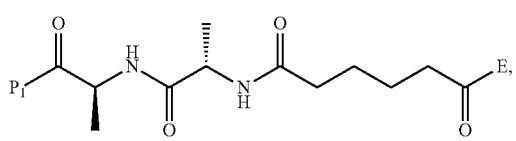

(a)

or a salt thereof, to form a compound of formula (IIa):

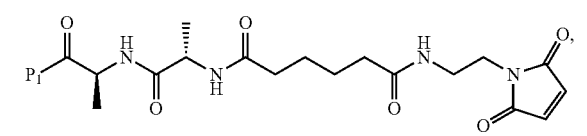

(IIa)

(b) reacting the compound of formula (IIa) with a carboxylic acid deprotecting agent to form the compound of formula (IIIa):

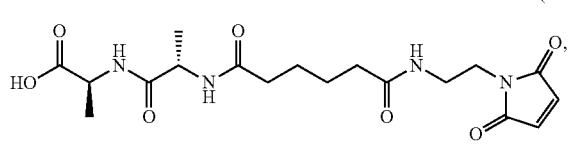

or a salt thereof; and (c) reacting the compound of formula (IIIa) with a compound of formula (IV):

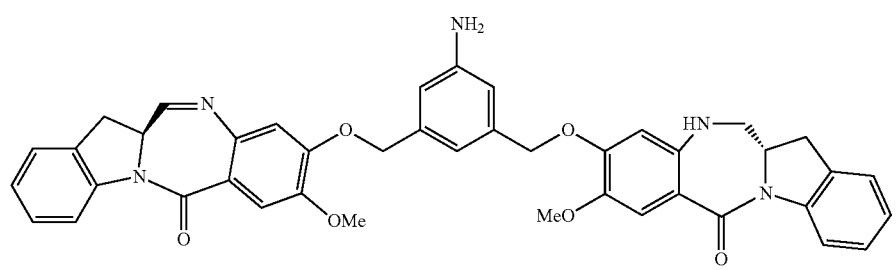

to form the compound of formula (Va), wherein E is —OH, halide or —C(=O)E is an activated ester; and $P_1$ is a carboxylic acid protecting group.

12. The method of claim 11, wherein $P_1$ is —O$^t$Bu, —OMe, —OBn, or —O-silyl.

13. The method of claim 12, wherein $P_1$ is —O$^t$Bu.

14. The method of claim 11, wherein E is —OH and the reaction between the compound of formula (Ia) and the compound of formula (a) is carried out in the presence of an activating agent.

15. The method of claim 14, wherein the activating agent is a 2,4,6-trialkyl-1,3,5,2,4,6-trioxatriphosphorinane 2,4,6-trioxide, carbodiimide, a uronium, an activated ester, a phosphonium, 2-alkyl-1-alkylcarbonyl-1,2-dihydroquinoline, 2-alkoxy-1-alkoxycarbonyl-1,2-dihydroquinoline, or alkylchloroformate.

16. The method of claim 15, wherein the activating agent is 2,4,6-tripropyl-1,3,5,2,4,6-trioxatriphosphorinane-2,4,6-trioxide.

17. The method of claim 11, wherein the carboxylic acid deprotecting agent in step (b) is an acid.

18. The method of claim 17, wherein the acid is trifluoroacetic acid (TFA).

19. The method of claim 11, wherein the method comprises the steps of:

(a) reacting a compound of formula (Ia1):

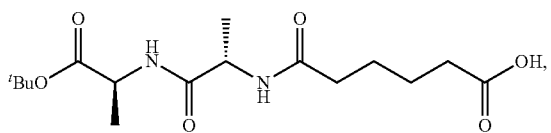

or a salt thereof, with a compound of formula (a):

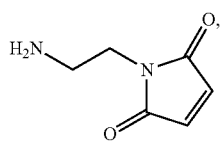

or a salt thereof, in the presence of an activating agent to form a compound of formula (IIa1):

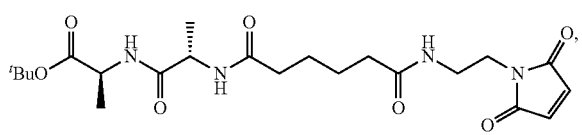

(b) reacting the compound of formula (IIa1) with a carboxylic acid deprotecting agent to form a compound of formula (IIIa):

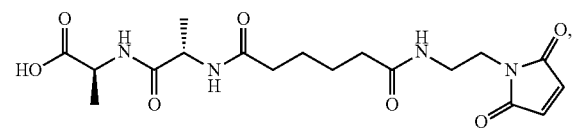

or a salt thereof; and (c) reacting the compound of formula (IIIa) with a compound of formula (IV):

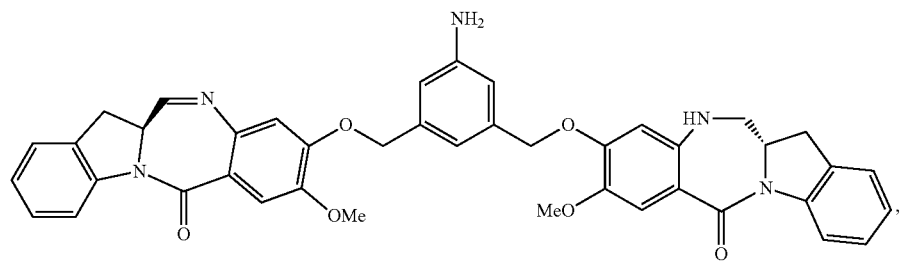
(IV)
to form the compound of formula (Va).
20. The method of claim 1, wherein E, when present, is —OH and the reaction in step (a) is carried out in the presence of an activating agent that is HATU and HOAt.
* * * * *